United States Patent [19]

Miyasaka et al.

[11] Patent Number: 4,956,345
[45] Date of Patent: Sep. 11, 1990

[54] 2-ALKYNYLADENOSINES AS ANTIHYPERTENSIVE AGENTS

[75] Inventors: Tadashi Miyasaka, Yokohama; Akira Matsuda, Sapporo; Toichi Abiru, Sawara; Haruhiko Machida, Choshi, all of Japan

[73] Assignee: Yamasa Shoyu Kabushiki Kaisha, Chiba, Japan

[21] Appl. No.: 282,892

[22] Filed: Dec. 12, 1988

Related U.S. Application Data

[63] Continuation of Ser. No. 924,345, Oct. 24, 1986, abandoned.

[30] Foreign Application Priority Data

Oct. 25, 1985 [JP] Japan .................................. 60-240137

[51] Int. Cl.$^5$ ...................... A61K 31/70; C07H 19/167
[52] U.S. Cl. ........................................ 514/46; 536/23; 536/24; 536/26
[58] Field of Search .............................. 536/23, 24, 26

[56] References Cited

PUBLICATIONS

Matsuda et al., (I), Chem. Pharm. Bull., vol. 33(4), pp. 1766–1769, 1985 (Apr.).
Matsuda, et al. II, Chem. Abstr., vol. 101, 23865d, 1984(7/6).
Matsuda et al. III, Chem. Abstr., vol. 103, 196359m, 1985, (Chem. Abstr. Report of Ref. R).
Matsuda et al. IV, Chem. Abstr., vol. 104, 101950f, 1985.
Marumoto et al., Chem. Pharm. Bull., vol. 23(4), pp. 759–774 (1975).
Angus et al., Br. J. Pharmac., vol. 41, pp. 592–599 (1971).
Goodman et al., "The Pharmacological Basis of Therapeutics", 6th ed., 1980, MacMillan Publishing Co., New York, p. 799.

*Primary Examiner*—John W. Rollins
*Assistant Examiner*—L. Eric Crane
*Attorney, Agent, or Firm*—Wenderoth, Lind & Ponack

[57] ABSTRACT

A 2-alkynyladenosine represented by general formula [I]:

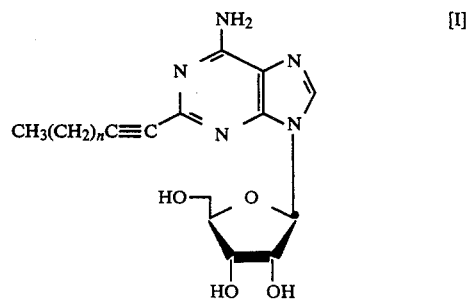

wherein n is an integer of from 2 to 15, has been found to have excellent properties as an antihypertensive agent. On the basis of this finding, the present invention has provided an antihypertensive agent comprising an antihypertensive effective amount of a compound of the above formula [I] and a pharmaceutically acceptable carrier. The present invention also discloses a novel compound 2-alkynyladenosine of formula [I] shown above wherein n is 6 to 15.

4 Claims, No Drawings

2-ALKYNYLADENOSINES AS ANTIHYPERTENSIVE AGENTS

This application is a continuation of now abandoned application Ser. No. 06/924,345, filed Oct. 24, 1986.

BACKGROUND OF THE INVENTION

The present invention relates to an antihypertensive agent comprising a 2-alkynyladenosine as an active ingredient.

Heretofore, adenosine has been used for the treatment of cardiac incompetency, myocardial infarction, arterial sclerosis and angina pectoris. This compound, however, exhibits a strong transient pharmacological effect when taken up into organisms and is known to be rapidly deaminated by adenosine deaminase or taken up into red blood cells and tissues to lose its activity. Adenosine also exhibits a strong suppressive effect on the heart as a side effect.

In order to improve the pharmacological activity of adenosine, impart thereto resistance to adenosine deaminase and mitigate undesirable side effects, a variety of adenosine analogues have been prepared synthetically.

With respect to 2-substituted adenosines, various compounds have been synthesized. For example, 2-alkylthioadenosines, 2-phenylaminoadenosines and the like exhibiting such physiological activities as adenosine deaminase inhibitor effect, coronary vasodilator effect, platelet aggregation inhibitor effect and antiviral effect have so far been obtained.

We have previously synthesized 2-alkynyladenosines of the following formula as 2-substituted adenosine derivatives each having a substituent introduced by a carbon-carbon bond in the 2 position of adenosine:

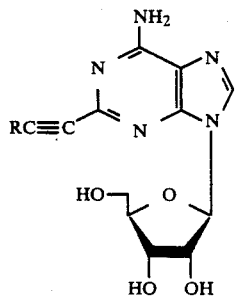

wherein R is $Si(CH_3)_3$, H, Ph, $CH_2OH$, $CH_2CH_2OH$, $CH(OH)CH_3$, $(CH_2)_2CH_3$, $(CH_2)_3CH_3$, $(CH_2)_4CH_3$ or $(CH_2)_5CH_3$, and have found that these compounds have an inhibitory effect on the $I_gE$-mediated 48-hr. passive cutaneous anaphylaxis reaction in rats. (Nucleic Acids Research Symposium Series No.12, pp. 5~8 (1983) and Chem. Pharm. Bull. Vol. 33, pp. 1766~1769 (1985)).

Numerous pharmaceutical preparations have been developed to date as antihypertensive agents. In view of the nature of the disease, pharmaceutical preparations must be administered over a long period of time in many cases. The intake of pharmaceutical preparations over a long period of time may sometimes induce drug resistance therefor or side effects. For this reason, stepwise pharmacotherapy is generally adopted so that a particular pharmaceutical is selected with due consideration for age, severity of hypertension, complications and the like and another pharmaceutical preparation having a different function mechanism is further used in combination depending upon the symptoms.

At present, no pharmaceutical preparations comprising compounds having adenosine skeletons are used as antihypertensive agents, and it would thus be highly profitable for the treatment of hypertension to provide antihypertensive agents comprising adenosine derivatives.

SUMMARY OF THE INVENTION

As a result of our intensive research directed to the development of novel 2-substituted adenosine derivatives useful as antihypertensive agents, we have found that 2-alkynyladenosines having an alkynyl group in the 2 position exhibit excellent antihypertensive properties. On the basis of this finding, we have arrived at the present invention.

More specifically, this invention provides an antihypertensive agent comprising an antihypertensive effective amount of a 2-alkynyladenosine represented by general formula [I]:

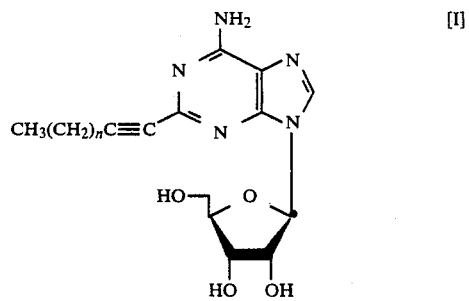

wherein n is an integer from 2 to 15, and a pharmaceutically acceptable carrier.

Among the 2-alkynyladenosines of the above formula [I] which form the active ingredients of the pharmaceutical preparations of the present invention, a 2-alkynyladenosine with a short-chain alkynyl substituent represented by formula [I-A] (hereinafter referred to as "short-chain alkynyl substituent compound"):

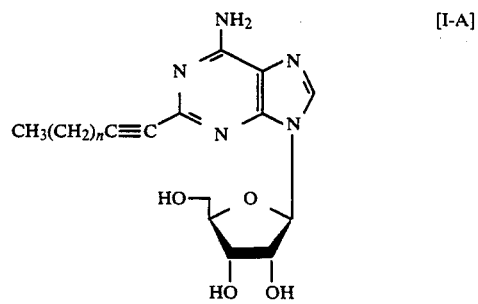

wherein n is an integer of from 2 to 5, is per se a known compound (ibid.) but a 2-alkynyladenosine with a long-chain alkynyl substituent represented by formula [I-B] (hereinafter referred to as "long-chain alkynyl substituent compound"):

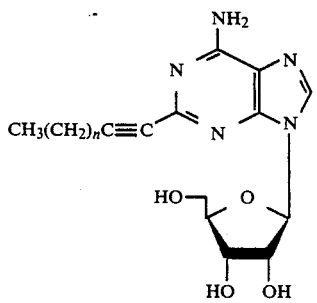

wherein n is an integer of from 6 to 15, is a novel compound. The present invention, therefore, also provides a novel 2-alkynyladenosine compound of the above formula [I-B].

DETAILED DESCRIPTION OF THE INVENTION

The 2-alkynyladenosine of the formula [I] shown supra which forms an active ingredient of the pharmaceutical preparation of the present invention can be synthesized by reacting a 2-halogenoadenosine of general formula [II]:

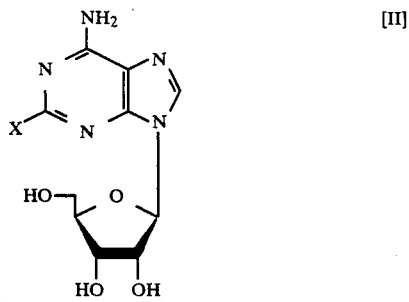

wherein X is iodine or bromine, with an alkyne of general formula [III]:

CH≡C[CH$_2$]$_n$CH$_3$     [III]

wherein n is an integer of from 2 to 15, in a solvent in the presence of bis(triphenylphosphine) palladium dichloride and cuprous iodide.

Depending upon the desired compound among those of the present invention, an alkyne having the corresponding "n" is selected.

For the solvent, basic solvents such as a solvent mixture of triethylamine and N,N-dimethylformamide are used. Triethylamine can be replaced by a tertiary amine such as tributylamine, trioctylamine, N,N,N',N'-tetramethyl-1,8-naphthalenediamine, dimethylaniline, diethylaniline or pyridine, while N,N-dimethylformamide can be replaced by a non-proton polar solvent such as N,N-dimethylacetamide, dimethyl sulfoxide or acetonitrile.

The reaction terminates in several hours at room temperature to solvent reflux temperature.

The compounds of the present invention can be isolated by any conventional separation and purification method. For example, adsorption chromatography, ion exchange chromatography, extraction or recrystallization is applied for the isolation.

The pharmaceutical preparations of the present invention are clinically utilized for the treatment of hypertension.

The pharmaceutical preparations of this invention are administered to patients orally, by injection, intrarectally or via topical administration. These preparations, when administered, are made by a conventional method into dosage forms suited for the desired route of administration. For example, solid form preparations such as tablets, powders, dragees, granules, sublingual tablets and capsules or liquid form preparations such as syrups, suspensions and elixirs are suitable for oral administration, injections for administration by means of a syringe, suppositories and ointments for intrarectal administration, and poultices for topical administration.

In the process of preparation, suitable additives such as binders, vehicles, lubricants, disintegrators, emulsifiers, suspending agents, antiseptics, stabilizers, solubilizing agents, taste conditioners, and sweeteners can be selected and used as necessary from a pharmaceutical point of view.

The optimum doses of the pharmaceutical preparations are determined according, for example, to the dosage form, severity of diseases, age and body weight.

For oral administration, for example, the pharmaceutical preparation comprising a short-chain 2-alkynyladenosine of the formula [I-A] as an active ingredient is administered to an adult generally at a dose level of the order of 0.1 to 5 mg/kg/day while that comprising a long-chain 2-alkynyladenosine of the formula [I-B] as an active ingredient is administered at a dose level of the order of 0.1 to 10 mg/kg/day.

The long-chain 2-alkynyladenosine, especially the compounds of the formula [I-B] wherein n is an integer of from 11 to 15, among the active ingredients of the pharmaceutical preparations of the present invention exhibits mild hypotensive effect of long duration coupled with relatively low toxicity and minimal side effects.

As a result of animal tests with normotensive rats (NR) and spontaneously hypertensive rats (SHR), the pharmaceutical preparations were further found to act on SHR selectively and barely affect normotension.

It has been found by us that also the known short-chain 2-alkynyladenosine has hypotensive effect, but shows more drastic hypotensive effect than the long-chain alkynyl substituent compound and acts equally on normotension while having higher toxicity.

In view of the foregoing, the long-chain 2-alkynyladenosine of the present invention can be said to be endowed with excellent properties that the known short-chain alkynyl substituent compound does not possess. It can also be said that, preferably, the short-chain 2-alkynyladenosine is used at lower dose levels than those for the long-chain alkynyl substituent compound.

EXAMPLES

Preparation of the compound of the present invention 6.0 g of 6-chloro-2-iodo-9-(2,3,5-tri-O-acetyl-β-D-ribofuranosyl) purine was added to 60 ml of methanol plus ammonia (saturated at 0° C.) to cause reaction at a temperature of 60° C. for 17 hours in a sealed tube. The reaction solution was cooled, then degassed, and concentrated under reduced pressure. Crystallization of the residue from water afforded 3.94 g of 2-iodoadenosine (90% yield) having a melting point of 141° C. to 144° C.

393 mg (1 mmole) of the 2-iodoadenosine was dissolved in 10 ml of dimethylformamide plus 3 ml of triethylamine, and to the solution obtained were added 21 mg of bis(triphenylphosphine) palladium dichloride and 12 mg of cuprous iodide. To the resulting solution was added an alkyne (1.1 equivalent) in an argon stream, and the mixture was stirred under heat at 80° C. After the reaction solution was concentrated under reduced pressure, the residue was dissolved in methanol, and hydrogen sulfide was passed through the solution for one minute. The precipitate formed was filtered off, and the filtrate was concentrated to dryness under reduced pressure. The residue was purified by column chromatography on silica gel and recrystallized from methanol or methanol-water to obtain 2-alkynyladenosine.

The reaction time, yield, melting point and infrared absorption spectrum are shown in TABLE 1.

TABLE 1

| Compound No. | Species of Alkynyl Group | Reaction Time (hr) | Yield (%) | Melting Point (°C.) | IR(KBr)cm$^{-1}$ $\nu C\equiv C$ |
| --- | --- | --- | --- | --- | --- |
| 1 | —C≡C(CH$_2$)$_2$CH$_3$ | 1 | 90 | 129–132 | 2230 |
| 2 | —C≡C(CH$_2$)$_3$CH$_3$ | 1 | 85 | 121–125 | 2230 |
| 3 | —C≡C(CH$_2$)$_4$CH$_3$ | 1 | 93 | 113–115 | 2230 |
| 4 | —C≡C(CH$_2$)$_5$CH$_3$ | 1 | 84 | 101–103 | 2230 |
| 5 | —C≡C(CH$_2$)$_7$CH$_3$ | 1 | 88 | 121–123 | 2230 |
| 6 | —C≡C(CH$_2$)$_9$CH$_3$ | 1 | 97 | 128–130 | 2230 |
| 7 | —C≡C(CH$_2$)$_{11}$CH$_3$ | 1 | 93 | 131–134 | 2230 |
| 8 | —C≡C(CH$_2$)$_{13}$CH$_3$ | 3 | 98 | 134–136 | 2230 |
| 9 | —C≡C(CH$_2$)$_{14}$CH$_3$ | 24 | 80 | 138–139 | 2230 |
| 10 | —C≡C(CH$_2$)$_{15}$CH$_3$ | 24 | 72 | 131–134 | 2230 |

TEST EXAMPLES

Test 1: Effect of the test compounds on the blood pressure in SHR

To twelve- to fifteen-week-old male SHRs were orally administered test compounds each suspended in 0.5% CMC/physiological saline at a rate of 2 ml/kg. The blood pressure of the thus treated SHRs was measured by means of a tail artery sphygmomanometer (supplied by Nalco Co., Model PE-300) prior to the oral administration and at 2, 4, 6 and 8 hours thereafter. Reduction in blood pressure was calculated on the basis of the values thus obtained, and the maximum reduction levels attained by the respective compounds are summarized in TABLE 2. Each test compound was evaluated with a group of 4 rats.

TABLE 2

| Compound No. | Dose (mg/kg) | Reduction in blood pressure ($-\Delta$max, mmHg) |
| --- | --- | --- |
| 2(n = 3) | 1 | >136 |
| 4(n = 5) | 1 | 69 |
| 5(n = 7) | 3 | 106 |
| 6(n = 9) | 3 | 65 |
| 7(n = 11) | 3 | 65 |
| 8(n = 13) | 3 | 48 |
| 9(n = 14) | 3 | 35 |
| 10(n = 15) | 3 | 46 |

As is apparent from TABLE 2, all Of the 2-alkynyladenosines exhibited hypotensive effect: the shorter the alkynyl substituent chain, the more drastic was the hypotensive effect while the longer the chain, the milder was the effect. Further, sedative effect was observed in the groups of rats administered with Compounds 2 to 4.

Test 2: Effect of the test compounds on the blood pressure in SHR

Thirty-two-week-old male SHRs (divided into groups of three rats each) were anesthetized with urethane (1.1 g/kg, i.p.), and the blood pressure of each of the rats delivered from the common carotid artery was recorded on a polygraph through a pressure transducer (Model MPU-0.5).

The pharmaceutical preparation was administered through a cannula inserted into the femoral vein of the rat at a rate of 0.5 ml/kg, and the blood pressure was measured continuously from before administration to 30 minutes after administration. The maximum levels of reduction in blood pressure were as set forth in TABLE 3.

TABLE 3

| Compound No. | Dose (μg/kg) | Reduction in blood pressure ($-\Delta$max, mmHg)Hg |
| --- | --- | --- |
| 6(n = 9) | 100 | 20 |
| 7(n = 11) | 100 | 21 |
| 8(n = 13) | 100 | 16 |

Test 3: Effect of the test compounds on the blood pressure in NR

The procedure of Test 2 was followed with 10- to 12-week-old male Wistar rats (divided into groups of three rats each) to measure the hypotensive effects of the respective pharmaceutical preparations (100 μg/kg). Simultaneously, the change in heart rate was measured. The heart rate was measured by an ictometer based on the systolic blood pressure as a trigger. The results obtained were as shown in TABLE 4.

TABLE 4

| Compound No. | Reduction in blood pressure ($-\Delta$max, mmHg) | Change in heart rate ($\Delta$HR) |
| --- | --- | --- |
| 1(n = 2) | 21 | −48 |
| 2(n = 3) | 42 | −36 |
| 3(n = 4) | 48 | −180 |
| 4(n = 5) | 55 | −288 |
| 5(n = 7) | 24 | −18 |
| 6(n = 9) | 26 | −12 |
| 7(n = 11) | 10 | 0 |
| 8(n = 13) | 5 | 0 |
| 9(n = 14) | 3 | −6 |
| 10(n = 15 | 10 | −5 |

From the data given in TABLE 4 it has been found that the long-chain alkynyl substituent compound wherein n is 11 or more has far less effect on the blood pressure of normotensive rats than the short-chain alkynyl substituent compound wherein n is 5 or less. It has also been noted that the long-chain compound has less influence on heart rate than the short-chain compound.

The overall results set forth in TABLES 3 and 4 show that Compound 6(n=9) exhibited substantially equal hypotensive effect on SHR and NR while Compounds 7(n=11) and 8(n=13) acted selectively on SHR.

Test 4: Effect of the test compounds on the blood pressure in SHR and NR

Eighteen- to twenty-week-old male SHR (divided into groups of four rats each) and eighteen- to twenty-week-old male Wistar rats (divided into groups of four rats each) were orally administered with Compound 8(n=13) in the same manner as in Test 2 at a dose of 10 mg/kg, and the blood pressure of each of the rats was measured. The results obtained are incorporated in TABLE 5.

TABLE 5

|  | Reduction in blood pressure ($-\Delta$, mmHg) | |
|---|---|---|
|  | 1 hr. after administration | 2 hrs. after administration |
| SHR | 41 | 42 |
| Wistar rat | 16 | 24 |

As is apparent from TABLE 5, the tendency of Compound 8(n=13) to act selectively on SHR was also observed in the case of oral administration.

Test 5: Acute toxicity

The acute toxicity of Compound 8(n=13) was tested with seven-week-old male Jcl:ICR mice.

The physically allowable doses of Compound 8 for intraperitoneal administration and oral administration were 800 mg/kg and 1,300 mg/kg, respectively.

None of the mice administered with the test compound at these maximum doses, divided into groups of five mice each, died, so that the $LD_{50}$ values for intraperitoneal administration and oral administration were estimated respectively at more than 800 mg/kg and more than 1,300 mg/kg.

When Compound 6(n=9) was tested by a similar procedure, on the other hand, all the five mice forming one group died with intraperitoneal administration of 500 mg/kg of the test compound.

As is noted from the above data, the effective amount of Compound 8 is 3 mg/kg while the $LD_{50}$ thereof is more than 1,300 mg/kg, indicating a 400-fold or higher safety coefficient. The longer-chain alkynyl substituent compound such as Compound 8 was thus found to be less toxic than the long-chain alkynyl substituent compound such as Compound 6.

FORMULATION EXAMPLES

Formulation 1: Tablets

A total of 150 mg of a mixture comprising 20 mg of a long-chain alkynyl substituent compound of the present invention, 90 mg of lactose, 24 mg of corn starch, 10 mg of hydroxypropyl cellulose, and 6 mg of magnesium stearate was kneaded with water, and the resulting mixture was granulated for tableting purposes by a conventional method. After drying, the granules thus obtained were mixed with magnesium stearate to make tablets which were then formed into desired shape. In the case of a short-chain alkynyl substituent compound, tablets were formed in the same manner except that the quantity of the compound used was 10 mg.

Formulation 2: Granules 40 mg of a long-chain alkynyl substituent compound of the present invention, 200 mg of mannitol and 50 mg of lactose were mixed. The mixture was kneaded with an aqueous solution containing 10 mg of polyvinyl alcohol, granulated and dried to obtain granules. In the case of a short-chain alkynyl substituent compound, granules were prepared in the same manner except that the quantity of the compound used was 20 mg.

Formulation 3: Capsules

Capsules were formulated by encapsulating the granules prepared for tableting purposes in Formulation 1.

We claim:

1. A method for treating hypertension in mammals suffering therefrom which comprises administering to such mammals an antihypertensive effective amount of a 2-alkynyladenosine represented by formula [I]:

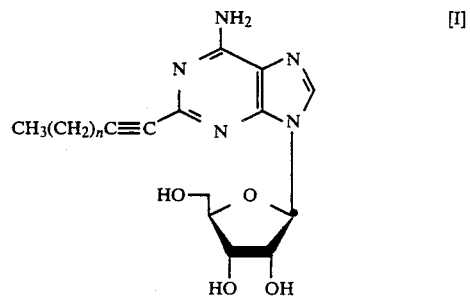

wherein n is an integer of from 2 to 15, and a pharmaceutically acceptable carrier.

2. A method according to claim 1 wherein n in the 2-alkynyladenosine of formula is an integer of from 2 to 5.

3. A method according to claim 1 wherein n in the 2-alkynyladenosine of formula is an integer of from 6 to 15.

4. A method according to claim 1 wherein n in the 2-alkynyladenosine of formula is an integer of from 11 to 15.

* * * * *